Jan. 22, 1974 MARIE-LOUISE MEILLAND Plant Pat. 3,452
ROSE PLANT
Filed Jan. 10, 1972
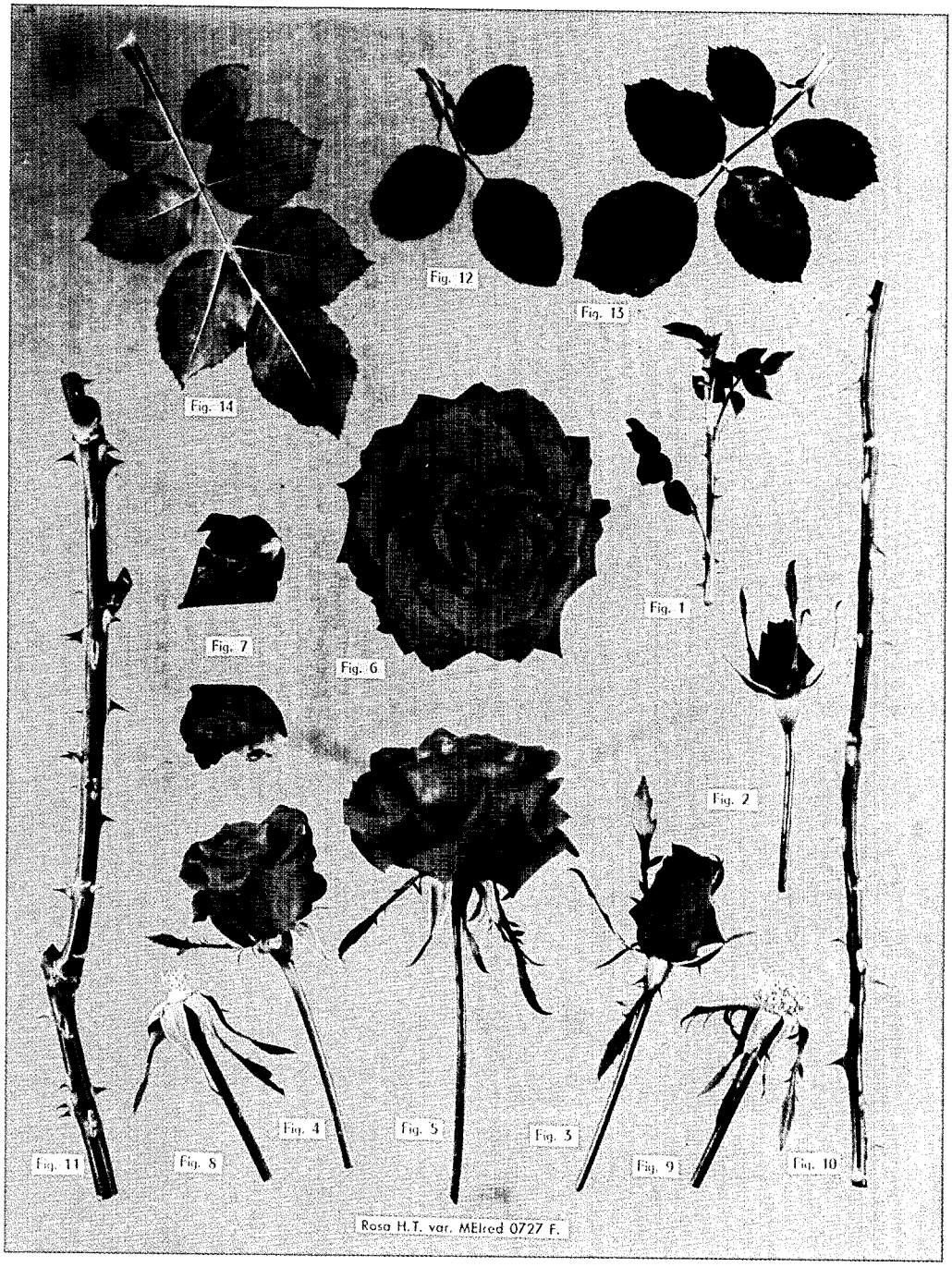

United States Patent Office

Plant Pat. 3,452
Patented Jan. 22, 1974

3,452
ROSE PLANT
Marie-Louise Meilland, Cap d'Antibes, France, assignor to The Conrad-Pyle Company, West Grove, Pa.
Filed Jan. 10, 1972, Ser. No. 216,817
Claims priority, application France, Jan. 15, 1971, 7102259
Int. Cl. A01h 5/00
U.S. Cl. Plt.—20 1 Claim

ABSTRACT OF THE DISCLOSURE

A rose plant of the hybrid tea class, with double red flowers, produced by crossing the variety Lovita (Plant Pat. No. 2,598), as pollen parent, on an unnamed seedling, as seed parent, which was the product of crossing Baccara (Plant Pat. No. 1,367) on Queen Elizabeth (Plant Pat. No. 1,257).

BACKGROUND OF THE DISCLOSURE

The object of the present invention is a variety of rose plant of the hybrid tea class, with double red flowers, which is distinguishable from varieties already known in that class and that kind of color, due to the following characteristics:

(1) Brightness and luminosity of the color of its flowers, more accentuated, especially under artificial light;

(2) Superior yield of the plant when forced, owing to its particularly vigorous and abundant vegetation, and to its capacity for sending forth strong shoots;

(3) Flowers lasting a very long time when cut.

Because of the characteristics mentioned above, the present invention answers the needs of the horticultural industry for the production of cut flowers, as well as all uses intended for the ornamentation of parks and gardens.

The aim which the applicant had in view was the creation of a variety which would derive the aforesaid advantages from the genetic combination of two genitors whose previous and respective study would allow her to expect, in their common descent, the appearance of the characters desired.

The rose chosen as female genitor (seed parent) was an unnamed seedling which was the product of the pollination of the variety Baccara (Plant Pat. No. 1,367), by the variety Queen Elizabeth (Plant Pat. No. 1,259). The rose chosen as male genitor (pollen parent) was the variety Lovita (Plant Pat. No. 2,598).

The operation of artificial pollination performed by the applicant is expressed by the following schematic formula:

(Baccara × Queen Elizabeth) × Lovita

From the fruits thus formed by this controlled pollination, seeds were extracted whose cells were the result of the combination of factors which existed in the cells of the genitors and in virtue of which these genitors had been precisely chosen.

After having sown the above-mentioned seeds, the applicant obtained 490 small plants, physically and biologically distinct from one another.

After having discarded all the plants which were deficient or abnormal, or whose characters were too remote from the ones she was seeking, the applicant proceeded with the grafting of the remaining plants, in order to carry on her work only on rose-plants which were, in every respect, in conformity with those produced and commercialized by professional nurserymen.

She then undertook the selective study of the individual plants thus formed; during this study, she was led to eliminate systematically all the rose-plants which had been grafted, with the exception of only one, which came the closest to the desired goal.

This rose plant was producing flowers of a remarkable bright and luminous red color; moreover, they lasted a very long time when cut. The vegetation of the plant was particularly vigorous and abundant, producing new strong shoots.

Technical tests (grafting inside or outside, with started eye-buds or dormant eye-buds, on different understocks, in heated or cold greenhouses, etc.) were then made in order to ascertain the behavior of the newly created variety. The results were conclusive and underlined the importance of creating this variety with the view to its industrial exploitation by horticulturists for the production of cut flowers, and by professional nurserymen for the ornamentation of parks and gardens.

The characters and properties of this new variety, obtained as indicated above, are thoroughly transmissible by asexual means, i.e. by any method of vegetative propagation, and in particular by grafting an "eye" and which will be found on individual plants as well as on cut stems delivered subsequently to the trade.

Asexual reproduction of this new variety by grafting and budding shows that its characteristics and distinctions come true to form and are transmitted through succeeding propagations.

BRIEF DESCRIPTION OF DRAWINGS

The accompanying drawings show typical specimens of the flowers and foliage of this new variety in different stages of development and as depicted in color as nearly true as is reasonably possible to make the same in a color illustration of this character, wherein:

FIG. 1 is a view of a specimen of a young shoot;

FIG. 2 is a view of a specimen of a bud when the sepals start to open;

FIG. 3 is a view of a specimen of a bud when the first petals open;

FIG. 4 is a view of a specimen of a flower when half open;

FIG. 5 is a view of a specimen of a flower in the course of opening;

FIG. 6 is a view of a specimen of a fully open flower, flat view;

FIG. 7 is a view of two specimens of petals when opening, blistered and distorted by a median rib somewhat even and pronounced;

FIG. 8 is a view of a specimen of receptacle showing the disposition of the pistils;

FIG. 9 is a view of a specimen of receptacle showing the disposition of the stamens;

FIG. 10 is a view of a portion of a flowering stem;

FIG. 11 is a view of a portion of a main branch;

FIG. 12 is a view of a specimen of leaf with three folioles, upper surface;

FIG. 13 is a view of a specimen of leaf with five folioles, upper surface; and

FIG. 14 is a view of a specimen of leaf with seven folioles, under surface.

DETAILED DESCRIPTION OF DISCLOSURE (The terminology of the colors corresponds to that of the Horticultural Color Chart of the Royal Horticultural Society.)

(A) *Greenhouse plants*

Class: Hybrid tea

Plant:

*Height.*—Stems starting from the base of the plant, up to a mature bud: 1.60 m. to 1.75 m. Stems branching out of the main stem, cut at about 1.30 m.: 1.80 m. to 2.10 m.

*Habit.*—Straight.

Branches:

*Color.*—Young stems: Spinach Green—187–0960/1 more or less tinted with reddish brown. Mature wood: Spinach Green—187–0960/1 and 0960/2.

*Prickles.* — Shape: straight — tapered — sometimes slightly bent towards the base—narow base, distended very little. Size: medium. Quantity: fairly numerous. Color: on young stems: greenish, sometimes tinted with red; on mature wood: light Havana (general term).

Leaves:

*Stipules.*—Adnate—pectinate—with very enveloping and fairly distended base. The auricles are fine and diverging.

*Petiole.*—Obverse: the edges of the rib are more or less reddish and ciliated with tiny glands, especially near the stipules; the interior is light green and sometimes slightly downy, particularly in the flat part where the stipules are adnate. Reverse: light green—smooth—sometimes one or several small curved prickles.

*Folioles.*—Number: 3—5—7 and sometimes 9; 2 of which very small. Shape: elliptical. Teeth: single—fairly well marked. Texture: of good consistency. General effect: fairly ample foliage, average density—shiny on young stems, dull on adult branches. Color: young foliage: upper surface: shiny bronze green (general term); under surface: dull light green (general term); mature foliage: upper surface: Spinach Green—187 darker than 0960, under surface: Spinach Green—187 lighter and "rawer" green than 0960/3.

It is to be noted than when growth starts, as also during the course of vegetation, the foliage of the young shoots is light green on the upper surface, and light green, more or less with a reddish brown pigment, on the under surface.

Inflorescence:

*Number of flowers.*—Generally one flower per stem.

*Peduncle.*—Very firm and nearly smooth. The length varies from 10 to 14 cms. It is Spinach Green—187—0960/2 and is slightly reddish near the receptacle.

*Sepals.*—Normal—more or less ciliated with minute glands—the sepals are tomentous and greenish white inside, smooth and light green outside—three out of five are fairly often appendiculate.

*Bud.*—Shape: first of all conical, then pointed and somewhat cylindrical when opening. Length: 3 cms. ½ outside the calyx. Size: medium. Color: When sepals open: Oxblood Red 191—00823/1 and 00823. When the first petals open: inside: Turkey Red 94–721, shiny, and with a velvety shade of Cardinal Red—168—822/1; outside: Cardinal Red—168–822/1; shaded with Chrysanthemum crimson—169–824/1.

Flower:

*Form.*—Elegant, full and high-centered, then rounded with petals overlapping, the center sometimes being quartered; double flower.

*Diameter.*—12 cms. on an average.

*Color.*—When opening: inside: Turkey Red 94–721/1 and 721/2, shiny with a velvety shade of Cardinal Red 168–822/3; outside: Cardinal Red 168–822/3, dull. During the course of opening: inside: Turkey Red—94–721 satin-like on the outer periphery; 721/2, dull on the inner periphery; outside: Cardinal Red 168–822/1, dull. When fully open: inside: Turkey Red 94–721/1, satiny on the outer periphery; 721/2 dull on the inner periphery; outside: Cardinal Red 168–822/3, dull.

*Fragrance.*—Light.

*Duration.*—Very long.

*Corolla.*—Petals: texture: very firm. Shape: except for the 4 or 5 first entire petals whose base is wide and enveloping, the others have a narrow base, with a rounded top, slightly folded up and indented. The first two petals generally show a median rib, of greenish white color, slightly tomentous, which gives them the appearance of being somewhat blistered. The unguis is yellowish. Number: 40 on an average, of which about ten, in the center, are not always entire. The petals drop off cleanly. Stamens: number: 90 average; anthers: normal—pale yellow. The edge of the cells containing the pollen is golden yellow. Filaments: of uneven length. They are fuchsine red from the base to the top. Pistils: Number: average 80; stigmas: normal—yellowish; styles: free—projecting—looking somewhat twisted—slightly tomentous up to half their length—yellowish at the base—more or less fuchsine red towards the stigmas. Receptacle: light green—in the shape of a goblet.

Development:

*Vegetation.*—Very vigorous.

*Yield capacity.*—Very big.

*Resistance to diseases.*—Excellent.

(B) *Open air plants*

(Below only the characteristics which differ from those of the greenhouse plants are given.)

Plant: Height: 0 m. 85 on an average.

Branches:

*Color.*—Young stems: the reddish brown pigmentation is more pronounced and spread than in the greenhouses.

*Prickles.*—Young stems: reddish.

Foliage:

*Folioles.*—Size: in general, a little smaller than that observed in the greenhouses. Texture: more leathery—very pronounced ribs.

Inflorescence:

*Peduncle.*—Looks a little rough. On the average, it is 10 cms. in length.

Development:

*Blooming.*—Abundant, continuous.

*Resistance.*—To spring frost: normal; to winter frost: very good; to fungus diseases: especially good.

*Aptitude for setting fruit.*—Medium to weak.

I claim:

1. A new and distinct variety of rose plant of the hybrid tea class substantially as herein shown and described, characterized particularly in that the plant, when mature, has Spanish Green wood, is erect, grows very vigorously, has a big yield capacity under glass, and has excellent resistance to fungus diseases, and the flower is double, Turkey Red inside, Cardinal Red outside, the petals are very firm and have a yellowish unguis, and the blooms last a very long time when cut.

No references cited.

ROBERT E. BAGWILL, Primary Examiner